United States Patent
Paul et al.

(10) Patent No.: US 7,087,763 B2
(45) Date of Patent: *Aug. 8, 2006

(54) PROCESS FOR PREPARATION OF ALKYLIMIDAZOLIDONE (METH)ACRYLATES

(75) Inventors: Jean-Michel Paul, Metz (FR); Bernard Dupont, Creutzwald (FR)

(73) Assignee: Atofina, Puteaux (FR)

( * ) Notice: Subject to any disclaimer, the term of this patent is extended or adjusted under 35 U.S.C. 154(b) by 54 days.

This patent is subject to a terminal disclaimer.

(21) Appl. No.: 10/738,940

(22) Filed: Dec. 15, 2003

(65) Prior Publication Data

US 2004/0147761 A1    Jul. 29, 2004

Related U.S. Application Data

(62) Division of application No. 10/225,731, filed on Aug. 22, 2002, now Pat. No. 6,706,887.

(30) Foreign Application Priority Data

Aug. 28, 2001   (FR)  ................................... 01 11178

(51) Int. Cl.
C07D 233/30      (2006.01)
(52) U.S. Cl. .................................. 548/324.1
(58) Field of Classification Search ............. 548/324.1
See application file for complete search history.

(56) References Cited

U.S. PATENT DOCUMENTS

| | | | |
|---|---|---|---|
| 477,252 A | 6/1892 | Pleadwell | |
| 5,037,978 A | 8/1991 | Mirabelli | |
| 5,210,199 A | 5/1993 | Grosius et al. | |
| 5,498,723 A | 3/1996 | Riondel et al. | |
| 5,567,826 A | 10/1996 | Knebel et al. | |
| 5,610,313 A | 3/1997 | Riondel et al. | |
| 5,637,689 A | 6/1997 | Herbst et al. | |
| 5,744,613 A | * 4/1998 | Riondel et al. | 548/324.1 |
| 5,883,261 A | 3/1999 | Esch et al. | |
| 6,147,252 A | 11/2000 | Nakamura et al. | |

FOREIGN PATENT DOCUMENTS

| | | |
|---|---|---|
| EP | 0 236 994 A1 | 9/1987 |
| EP | 0 433 135 B1 | 6/1991 |
| EP | 0 447 141 A2 | 9/1991 |
| EP | 0 453 638 A1 | 10/1991 |
| EP | 0 571 851 A1 | 12/1993 |
| EP | 0 619309 B1 | 6/1994 |
| EP | 0 712846 B1 | 3/1997 |
| EP | 0 902027 A1 | 3/1999 |
| EP | 0 968995 A1 | 1/2000 |

OTHER PUBLICATIONS

French Search Report for French Application No. 01 11 178.

* cited by examiner

Primary Examiner—Kamal A. Saeed
Assistant Examiner—Robert Shiao
(74) Attorney, Agent, or Firm—Welsh & Katz, Ltd.

(57) ABSTRACT

The invention relates to a process for the preparation of alkylimidazolidone (meth)acrylates, generally expressed as compound (I):

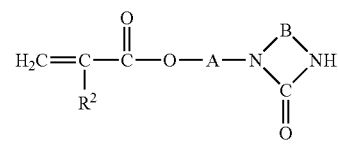

that are prepared by reacting at least one (meth)acrylate of formula (II):

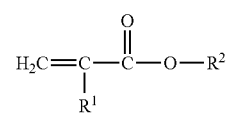

with a heterocyclic alcohol of formula (III):

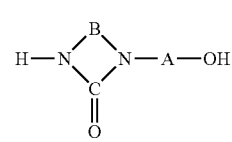

in the presence of a catalyst comprising at least one compound (a) which is a chelate formed of lithium and of a 1,3-dicarbonyl compound. The invention also relates to a composition comprising compound (I) in solution in (meth)acrylate (II). Finally, the invention involves the use of the abovementioned composition in the preparation of polymers that can be used as coatings and adhesives, in the treatment of paper and of textiles, as agent for leather treatment and in the production of paints with high wet adhesion characteristics.

2 Claims, No Drawings

PROCESS FOR PREPARATION OF ALKYLIMIDAZOLIDONE (METH)ACRYLATES

CROSS-REFERENCE TO RELATED APPLICATIONS

This Application is a divisional of and claims the benefit of priority from application Ser. No. 10/225,731, now is U.S. Pat. No. 6,706,887, filed Aug. 22, 2002, entitled Process For The Preparation Of Alkylimidazolidone(Meth)Acrylates, and currently pending, which claims benefit of priority from French Patent Application No. 01 11 178 filed Aug. 28, 2001.

FIELD OF THE INVENTION

The present invention relates to a process for the preparation of alkylimidazolidone (meth)acrylates.

BACKGROUND

Alkylimidazolidone acrylates and methacrylates are known for their role in the constitution of polymers which can be used as coatings and adhesives, in the treatment of paper and of textiles, for their use as agents for leather treatment and in the production of emulsion paints.

European patent application No. 236 994 relates to the preparation of esters of (meth)acrylic acid by reacting an alkyl (meth)acrylate with a heterocyclic alcohol in the presence of a catalyst that is a titanium alkoxide or a titanium, zirconium, iron or zinc chelate, combined with a 1,3-dicarbonyl compound, which may be a metal chelate of a 1,3-diketone, in particular an acetylacetonate.

Such a catalyst has the major disadvantage of generating intensely coloured products.

European patent application No. 433 135 relates to a process for the synthesis of an alkylimidazoline (meth)acrylate, in which an alkyl (meth)acrylate is reacted with a heterocyclic alcohol in the presence of a catalyst chosen from dialkyl tin oxides, dialkyl tin dialkoxides and dialkyl tin diesters.

Such a catalyst requires high reaction temperatures and often causes violent polymerizations with formation of a very hard expanded polymer.

European patent application No. 453 638 also relates to the synthesis of an alkylimidazoline (meth)acrylate in the presence of dialkyl tin oxide.

The subject of European patent application No. 571 851 is a process for the preparation of alkylimidazoline (meth)acrylate, by transesterification of an alkyl (meth)acrylate by means of a heterocyclic alcohol, in the presence of a catalytic system which is a combination of a catalyst based on lithium, for example in oxide, alkoxide, acetate, chloride or bromide form, and a catalyst based on calcium, such as calcium oxide.

European patent application No. 619 309 relates to the preparation of alkylimidazoline (meth)acrylate by reacting an alkyl (meth)acrylate with a heterocyclic alcohol in the presence of a catalyst chosen from the chelates of calcium with 1,3-dicarbonyl compounds, such as calcium acetylacetonate. The products obtained by the process described in that document has an excessively strong colour.

Finally, European patent application No. 902 017 mentions the use of a catalyst that may be lithium, lithium carbonate or lithium hydroxide in the preparation of a monomer from, in particular, hydroxyethyloxazolidine and methyl methacrylate.

However, the use of such catalytic systems does not make it possible to simultaneously achieve the following main objectives:
- a high conversion of the heterocyclic alcohol;
- a low content of by-products;
- a high kinetic;
- a low thermal level; and
- a faint colouring of the final product.

The subject of the invention is a process for the preparation of alkylimidazoline (meth)acrylate, a process which makes it possible to achieve the objectives mentioned above.

Specifically, the subject of the invention is a process for the preparation of compound (I):

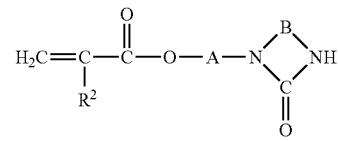

wherein:
$R^1$ is a hydrogen atom or a methyl group; and
A and B represent, independently of each other, a straight- or branched-chain alkylene group having from 2 to 5 carbon atoms;
by reacting at least one (meth)acrylate (II):

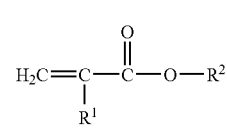

wherein:
$R^1$ has the abovementioned meaning; and
$R^2$ is a straight- or branched-chain alkyl group having from 1 to 4 carbon atoms;
with a heterocyclic alcohol (III):

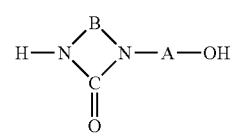

wherein A and B have the abovementioned meanings;
in the presence of a catalyst comprising at least one compound (a) which is a chelate formed of lithium and of a 1,3-dicarbonyl compound.

The subject of the invention is also a composition comprising compound (I) obtained by the process according to the invention in solution in (meth)acrylate (II).

Finally, the subject of the invention is also the use of the abovementioned composition in the preparation of polymers that can be used as coatings and adhesives, in the treatment of paper and of textiles, as agent for leather treatment and in the production of paints with high wet adhesion characteristics.

DETAILED DESCRIPTION

The preparation process according to the invention, as has been described above, makes use of a catalyst comprising at least one compound (a) which is a chelate formed of lithium and of a 1,3-dicarbonyl compound.

Examples of 1,3-dicarbonyl compounds include but are not limited to the following:

a α-ketonic acid ester, such as acetylacetic ester;
a 1,3-diketone, such as acetylacetone, 3-methylacetylacetone, benzoylacetone, dibenzoylmethane, 2,4-hexanedione, 3,5-heptanedione, 3-phenylacetylacetone, 4,4,4-trifluoro-1-phenyl-1,3-butanedione, 2,2,6,6-tetramethyl-3,5-heptanedione, 1,1,1-trifluoro-5,5-dimethyl-2,4-hexanedione and 1,1,1-trifluoro-2,4-pentanedione.

Lithium acetylacetonate is most particularly preferred as compound (a).

Examples of reagent (II) include, but are not limited to, methyl, ethyl, n-propyl, isopropyl, n-butyl and isobutyl acrylates and methacrylates.

Preferably, reagent (II) is methyl methacrylate or acrylate.

An example of reagent (III) is 1-(2-hydroxyethyl)imidazolidyl-2-one, among others.

The quantity of compound (a) used for carrying out the process according to the invention is usually defined relative to the quantity of heterocyclic alcohol.

Thus, the molar ratio of compound (a) to the heterocyclic alcohol (III) is generally between 0.05 and 0.3 percent, and preferably between 0.05 and 0.15 percent.

In an advantageous variant of the process according to the invention, compound (a) is not used alone as catalyst, but rather in the form of a mixture together with a second compound (b). Computer (b) may be chosen from magnesium alkoxides, sodium alkoxides, calcium alkoxides, calcium acetylacetonate, calcium oxide and calcium hydroxide.

As alkoxides, examples include methoxides, ethoxides, propoxides, isopropoxides, butoxides and isobutoxides.

With regard to the quantity of compound (b), it may be less than that of compound (a).

Typically, the quantity of compound (b) is chosen such that the molar ratio of compound (b) to the heterocyclic alcohol (III) is between 0.01 and 0.1 percent, and preferably between 0.01 and 0.05 percent.

The reaction between reagent (II) and reagent (III) is generally carried out in the presence of an excess of either of these reagents.

It is, however, preferable to use more of reagent (II) than reagent (III).

Thus, it is desirable that the molar ratio of the (meth)acrylate (II) to the heterocyclic alcohol (III) is greater than 1, preferably between 1.1 and 7, more preferably between 2 and 5.

In this manner, a composition comprising a solution of compound (I) in (meth)acrylate (II) is obtained as the product of the reaction, for example:

a solution of 1-ethylimidazolidyl-2-one acrylate in methyl acrylate; or alternatively
a solution of 1-ethylimidazolidyl-2-one methacrylate in methyl methacrylate.

Such a composition, which has a colour of less than 100 APHA, may be advantageously used directly in certain applications such as the manufacture of paints with high wet adhesion characteristics, the treatment of leather or the manufacture of coatings.

The process according to the invention may be carried out in the presence of one or more polymerization inhibitors, which may be chosen from phenothiazine, hydroquinone, the monomethyl ether of hydroquinone, di-tert-butyl-para-cresol, para-phenylenediamine, TEMPO (2,2,6,6-tetramethyl-1-piperidinyloxy) and di-tert-butylcatechol.

These compounds may be optionally combined with metal chelators such as EDTA, oxalic acid or the products marketed under the trademark VERSENEX.

The content of polymerization inhibitor is generally between 0.05 and 0.5%, this percentage being expressed as weight of inhibitor (to which the weight of the associated chelator(s) is added where appropriate) relative to the weight of heterocyclic alcohol (III).

Regarding the operating conditions, the process is usually carried out at a temperature of between 70 and 120° C., and preferably between 85 and 100° C., in liquid medium.

The pressure is in general at most equal to 1 bar; it is typically between 0.3 and 1 bar.

It is advantageous to carry out the reaction with bubbling air.

The duration of the reaction depends on the operating conditions and the activity of the catalyst. It is generally between 6 and 11 hours.

The reaction is desirably carried out in an anhydrous medium in order to avoid the deactivation of the catalysts.

The water present in the reagents is preferably removed by distillation in the form of an azeotrope of (meth)acrylate (II) and water.

The procedure may be briefly described as follows.

A mixture of the reagents (II) and (III) and of the inhibitor(s) is heated under reflux, while adjusting the pressure in the installation so that the temperature in the reactor is maintained between 85 and 100° C.

The column is stabilized by introducing one or more polymerization inhibitors at the top of the column, in the reflux.

The water present in reagents (II) and (III) and the inhibitor is removed by distillation in the form of an azeotrope with the (meth)acrylate (II).

The catalyst(s) is(are) then introduced.

The reaction is carried out with generation of the alcohol $R^2OH$, which is removed by formation of an azeotrope with the (meth)acrylate (II), in order to displace the equilibrium of the transesterification reaction.

Thus, the equilibrium of the transesterification reaction is displaced in the direction of the formation of compound (I).

Throughout the duration of the reaction, the pressure is adjusted in order to maintain the temperature inside the reactor between 85 and 100° C.

If necessary, catalyst(s) is(are) supplied during the reaction.

When no further alcohol $R^2OH$ is formed, the reaction may be considered to be complete.

The crude product obtained is then cooled and extracted from the reactor. It is generally in the form of a clear and very slightly coloured liquid (colour less than 100 APHA).

Any excess of (meth)acrylate may then be removed by evaporation (so-called stripping operation), so as to isolate compound (I) from the reaction medium, generally in the solid state: thus, the 1-ethylimidazolidyl-2-one acrylate is a white crystalline solid having a melting point equal to 43° C., which is soluble in the cold state in ketones, alcohols, aromatic hydrocarbons and water, insoluble in the cold state in saturated hydrocarbons and which precipitates at 0° C. from ethyl acrylate. 1-Ethylimidazolidyl-2-one methacrylate is a white crystalline solid having a melting point equal to 47° C., possessing the same solubility properties as the preceding compound. At the end of the stripping operation, the crystalline solid product may in addition be purified by washing with a light alcohol such as methanol and/or with a petroleum ether, followed by filtration and drying.

The isolation of compound (I) may also be carried out by partial stripping of the (meth)acrylate (II), followed by crystallization at a sufficiently low temperature (preferably of less than or equal to 0° C.) and for a sufficiently long period (which may be up to 15 hours), and then filtration followed by the purification steps described above.

Finally, another method for isolating compound (I) from the solution containing it consists of carrying out an extraction with water, followed by decantation, stripping of the (meth)acrylate and the purification steps described above.

EXAMPLES

The following examples illustrate the present invention without, however, limiting the scope thereof.

The following abbreviations are used therein:

| | |
|---|---|
| MMA: | methyl methacrylate |
| HEIO: | 1-(2-hydroxyethyl)imidazolidyl-2-one |
| EIOM: | 1-ethylimidazolidyl-2-one methacrylate |
| MEHQ: | monomethyl ether of hydroquinone |
| PTZ: | phenothiazine |
| Li(acac): | lithium acetylacetonate |
| Ca(acac)$_2$: | calcium acetylacetonate |
| DBTO: | dibutyltin oxide |

Examples 1 to 3

Into a jacketed 630-litre stainless steel reactor supplied with a thermofluid, equipped with a mechanical stirrer and surmounted by a distillation column (diameter 250 mm, height 4 m), filled with a PALL packing and surmounted by a reflux head, are introduced:

150 kg of HEIO;
461 kg of MMA; and
0.2 kg of PTZ (polymerization inhibitor).

The column is stabilized by introducing into the reflux a solution of MEHQ at 0.1% by weight in MMA.

The reaction mixture is dried by azeotropic distillation of the water contained in the reagents (the azeotrope being formed between the MMA and the water) under a pressure of 400 mmHg (the temperature at the top of the column is 77° C.).

When the drying step is complete, the catalyst(s) is(are) introduced and additional methyl methacrylate is added in order to maintain the MMA/EIOM molar ratio at its initial value of 4/1.

Throughout the duration of the reaction, the pressure is adjusted in order to maintain the temperature in the reactor at 85° C.

The methanol formed by the reaction is removed in the form of an azeotrope with the MMA.

The reaction is complete when the temperature at the top of the column no longer falls towards that of the azeotrope, in total reflux, at the operating pressure.

The crude product is then cooled and analysed by HPLC.

The colour of the crude product is an important factor. It should be as faint as possible.

Examples 1 to 3 of the following Table A were all performed under the above conditions, by varying the nature of the catalyst(s). Example 2, outside the scope of the invention, was performed for the sake of comparisons: the catalyst does not contain compound (a).

It is therefore seen that the EIOM yields are comparable for Examples 1 to 3. Nevertheless, the catalyst of Comparative Example 2 gives a final product having a strong colour.

TABLE A

| Example | Catalyst and mol % relative to the HEIO | Duration of the reaction in hours | Colour of the crude Product in APHA |
|---|---|---|---|
| 1 | Li(acac): 0.15 | 10 | 41 |
| 2 (comp.) | Ca(acac)$_2$: 0.15 | 10 | 100 |
| 3 | Li(acac) and Ca(acac)$_2$ 0.15 and 0.10 (respectively) | 8 | 74 |

| | Composition of the crude product (% by mass) | | |
|---|---|---|---|
| Example | MMA % | HEIO % | EIOM % |
| 1 | 57.8 | 1.2 | 33.3 |
| 2 (comp.) | 58.7 | 1.4 | 35.7 |
| 3 | 58.4 | 1.1 | 34.5 |

Examples 4 to 9

Trials were carried out in a small jacketed glass reactor which is mechanically stirred and surmounted by a glass distillation column, containing a "multiknit" packing (efficiency of 8 theoretical plates) and provided with a reflux head.

The general conditions are identical to those of Examples 1 to 3, the only exception being the MMA/HEIO molar ratio which is now 3.5/1 (instead of 4/1 previously).

Examples 5, 6 and 7, outside the scope of the invention, were performed for the sake of comparison: their catalysts do not contain compound (a).

The results are presented in the following Table B.

It is therefore seen that the catalysts of the Comparative Examples 5, 6 and 7 free of compound (a) give a strongly coloured final product.

TABLE B

| Example | Catalyst and mol % relative to the HEIO | Duration of the reaction in hours | Colour of the crude Product in APHA |
|---|---|---|---|
| 4 | Li(acac): 0.2 | 7.5 | 50 |
| 5 (comp.) | DBTO: 1.3 | 15 | 150 |
| 6 (comp.) | Zr(acac)$_2$ 0.2 | 8 | 120 |
| 7 (comp.) | Ca(acac)$_2$: 0.2 | 6 | 110 |
| 8 | Li(acac) and Ca(acac)$_2$ 0.2 and 0.1 (respectively) | 6.5 | 70 |
| 9 | Li(acac) and Mg(OEt)$_2$ 0.2 and 0.1 (respectively) | 7 | 80 |

| | Composition of the crude product (% by mass) | | |
|---|---|---|---|
| Example | MMA % | HEIO % | EIOM % |
| 4 | 50.2 | 1.0 | 40.8 |
| 5 (comp.) | 52.9 | 0.6 | 49.6 |

TABLE B-continued

| 6 (comp.) | 51.5 | 0.3 | 44.5 |
|---|---|---|---|
| 7 (comp.) | 51.8 | 1.7 | 38.7 |
| 8 | 50.7 | 1.2 | 40.2 |
| 9 | 50.2 | 1.8 | 39.2 |

What is claimed is:

1. Compositions comprising a compound (I):L

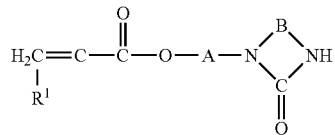
I wherein:
R$^1$ is a hydrogen atom or a methyl group; and
A represents a straight- or branched-chain alkylene group having from 2 to 5 carbon atoms;
B represents a straight- or branched-chain alkylene group having from 2 to 5 carbon atoms, and only two carbon atoms are in the ring of formula (I);
said compositions prepared with the compound (1) prepared by the process of reacting at least one (meth)acrylate of formula (II):

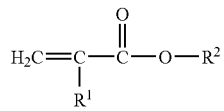
II wherein:
R$^1$ has the abovementioned meaning; and
R$^2$ is a straight- or branched-chain alkyl group having from 1 to 4 carbon atoms;
with a heterocyclic alcohol of formula (III):

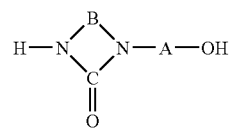
III wherein A and B have the abovementioned meanings;
in solution in (meth)acrylate of formula (II) in the presence of a catalyst comprising at least one compound (a) which is a chelate formed of lithium and of a 1,3-dicarbonyl compound.

2. The compositions according to claim 1, the colour of which is less than 100 APHA.

* * * * *